(12) United States Patent
Park

(10) Patent No.: US 9,267,899 B2
(45) Date of Patent: Feb. 23, 2016

(54) CONTAMINANT MEASUREMENT SUBSTRATE, APPARATUS AND METHOD FOR FABRICATING SUBSTRATE USING THE SAME

(71) Applicant: Samsung Display Co., Ltd., Yongin, Gyeonggi-Do (KR)

(72) Inventor: Chong Jin Park, Asan-si (KR)

(73) Assignee: SAMSUNG DISPLAY CO.,LTD (KR)

(*) Notice: Subject to any disclaimer, the term of this patent is extended or adjusted under 35 U.S.C. 154(b) by 156 days.

(21) Appl. No.: 14/099,978

(22) Filed: Dec. 8, 2013

(65) Prior Publication Data

US 2015/0026945 A1 Jan. 29, 2015

(30) Foreign Application Priority Data

Jul. 25, 2013 (KR) ........................ 10-2013-0088059

(51) Int. Cl.
| | |
|---|---|
| H01L 51/56 | (2006.01) |
| G01N 21/88 | (2006.01) |
| G01N 21/95 | (2006.01) |
| G01N 21/94 | (2006.01) |
| H01L 51/00 | (2006.01) |

(52) U.S. Cl.
CPC ................ *G01N 21/95* (2013.01); *G01N 21/94* (2013.01); *H01L 51/0096* (2013.01); *G01N 2021/9513* (2013.01); *Y10T 29/49764* (2015.01); *Y10T 29/51* (2015.01); *Y10T 428/24802* (2015.01)

(58) Field of Classification Search
CPC ............... G01N 2021/9513; G01N 2021/94; G01N 2021/95; H01L 51/56
See application file for complete search history.

(56) References Cited

U.S. PATENT DOCUMENTS

2013/0201460 A1* 8/2013 Tani ............................. 355/30

FOREIGN PATENT DOCUMENTS

| JP | 10-249295 A | 9/1998 |
|---|---|---|
| KR | 1020120081647 A | 7/2012 |
| KR | 1020120097890 A | 9/2012 |

* cited by examiner

*Primary Examiner* — Mark R Gaworecki
(74) *Attorney, Agent, or Firm* — Cantor Colburn LLP

(57) ABSTRACT

An apparatus for fabricating a substrate includes a chamber providing a space in which processes are performed, a contaminant measurement substrate including a base material configured to collect contaminants, and laser marks on the base material and defining coordinates of the base material, a first stage disposed inside the chamber, and upon which the contaminant measurement substrate is seated during collection of the contaminants of the chamber, a second stage disposed outside the chamber, and upon which the contaminant measurement substrate is seated during measurement of the contaminants of the chamber collected on the contaminant measurement substrate, and a contaminant measurement light source disposed on an upper portion of the second stage and configured to irradiate the contaminant measurement substrate seated on the second stage with light during the measurement of the contaminants of the chamber collected on the contaminant measurement substrate.

20 Claims, 15 Drawing Sheets

CONTAMINANT MEASUREMENT SUBSTRATE, APPARATUS AND METHOD FOR FABRICATING SUBSTRATE USING THE SAME

This application claims priority to Korean Patent Application No. 10-2013-0088059, filed on Jul. 25, 2013, and all the benefits accruing therefrom under 35 U.S.C. §119, the disclosure of which is incorporated herein in its entirety by reference.

BACKGROUND

1. Field

The invention relates to a contaminant measurement substrate, an apparatus and a method for fabricating a substrate using the same.

2. Description of the Prior Art

A substrate for a display device such as an organic light emitting display ("OLED"), a liquid crystal display ("LCD"), or a plasma display is fabricated as a completed product by fabricating processes.

The fabricating processes include a substrate thin-film deposition process, a coating process, and an assembling process, and are performed in respective process chambers.

While a substrate for a display device is processed by the fabricating processes, contaminants which occur due to splitting or aging of portions of the process chambers may often adsorb to the substrate.

SUMMARY

When a number of contaminants that adsorb to a substrate for a display device exceeds a reference value, inferiority may occur in the substrate for a display device that is fabricated as a completed product.

Accordingly, it is necessary to remove a cause of the occurrence of the contaminants by grasping a quantity of the contaminants in respective process chambers and locations of portions of the respective process chambers where the contaminants occur, before fabricating processes for the substrate for a display device are performed.

Exemplary embodiments of the invention provide a contaminant measurement substrate, which can effectively prevent inferiority of a substrate that passes through actual processes, using measuring of contaminants of a chamber before the actual processes of the substrate, grasping of the occurrence position of the contaminants and removing of the occurrence cause of the contaminants.

Another exemplary embodiment of the invention provide an apparatus for fabricating a substrate, which can effectively prevent inferiority of a substrate that passes through actual processes, using measuring of contaminants of a chamber before the actual processes of the substrate, grasping of the occurrence position of the contaminants and removing of the occurrence cause of the contaminants.

Another exemplary embodiment of the invention provide a method for fabricating a substrate, which can effectively prevent inferiority of a substrate that passes through actual processes, by measuring of contaminants of a chamber before the actual processes of the substrate, grasping of the occurrence position of the contaminants and removing of the occurrence cause of the contaminants.

According to an exemplary embodiment of the invention, there is provided an apparatus for fabricating a substrate including a chamber providing a space in which processes are performed, a first stage disposed inside the chamber, a contaminant measurement substrate including a base material configured to collect contaminants and laser marks on the base material and defining coordinates of the base material, a first stage disposed inside the chamber, and upon which the contaminant measurement substrate is seated during collection of the contaminants of the chamber, a second stage disposed outside the chamber, and upon which the contaminant measurement substrate is seated during measurement of the contaminants of the chamber collected on the contaminant measurement substrate, and a contaminant measurement light source disposed on an upper portion of the second stage and configured to irradiate the contaminant measurement substrate seated on the second stage with light during the measurement of the contaminants of the chamber collected on the contaminant measurement substrate.

According to another exemplary embodiment of the invention, there is provided a method for fabricating a substrate including preparing a contaminant measurement substrate including a base material configured to collect contaminants and laser marks on the base material and defining a plurality of unit areas on the contaminant measurement substrate respectively corresponding to unit cells of the substrate, seating the contaminant measurement substrate on a first stage which is disposed inside a chamber that provides a space in which processes are performed, and collecting the contaminants of the chamber, seating the contaminant measurement substrate on a second stage that is disposed outside the chamber, and measuring the contaminants of the chamber that are collected with respect to the plurality of unit areas by irradiating the contaminant measurement substrate with light using a contaminant measurement light source, and comparing a number of the contaminants of the chamber, which exist in a respective unit area among the plurality of unit areas that correspond to a respective unit cell of the substrate, with a reference value, and determining whether the number of the contaminants of the chamber existing in the respective unit area exceeds the reference value.

According to another exemplary embodiment of the invention, there is provided a contaminant measurement substrate including a base material configured to collect contaminants, and laser marks on the base material and defining coordinates of the base material.

According to exemplary embodiments of the invention, at least the following effects can be achieved.

Since the contaminant measurement substrate according to an exemplary embodiment of the invention includes the base material that can collect the contaminants and the laser marks that define the coordinates provided on the base material, the contaminants of the chamber can be measured before the actual processes of the substrate, the occurrence position of the contaminants can be grasped, and the occurrence cause of the contaminants of the chamber can be removed.

Accordingly, the contaminant measurement substrate according to an embodiment of the invention can effectively prevent the inferiority of the substrate that passes by the actual processes.

The effects according to the invention are not limited to the contents as exemplified above, but more various effects are described in the specification of the invention.

BRIEF DESCRIPTION OF THE DRAWINGS

The above and other objects, features and advantages of the invention will be more apparent from the following detailed description taken in conjunction with the accompanying drawings, in which.

DETAILED DESCRIPTION

Figure 1:
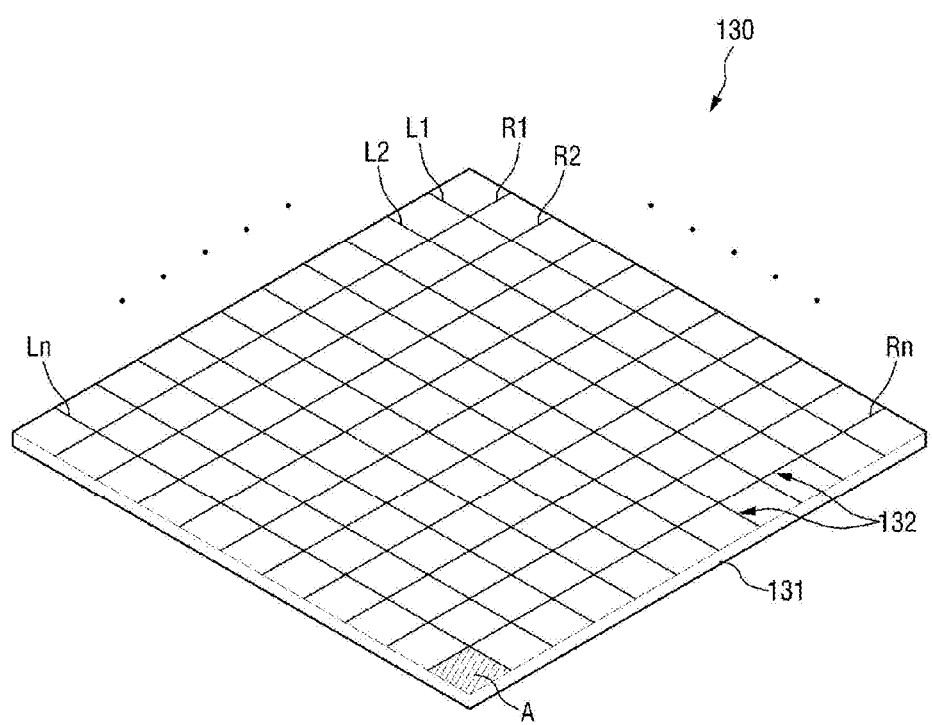
FIG. 1 is a perspective view of an exemplary embodiment of a contaminant measurement substrate according to the invention.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will also be understood that when a layer is referred to as being "on" another layer or substrate, it can be directly on the other layer or substrate, or intervening layers may also be present. The same reference numbers indicate the same components throughout the specification.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Hereinafter, exemplary embodiments of the invention will be described in detail with reference to the accompanying drawings.

Figure 2:
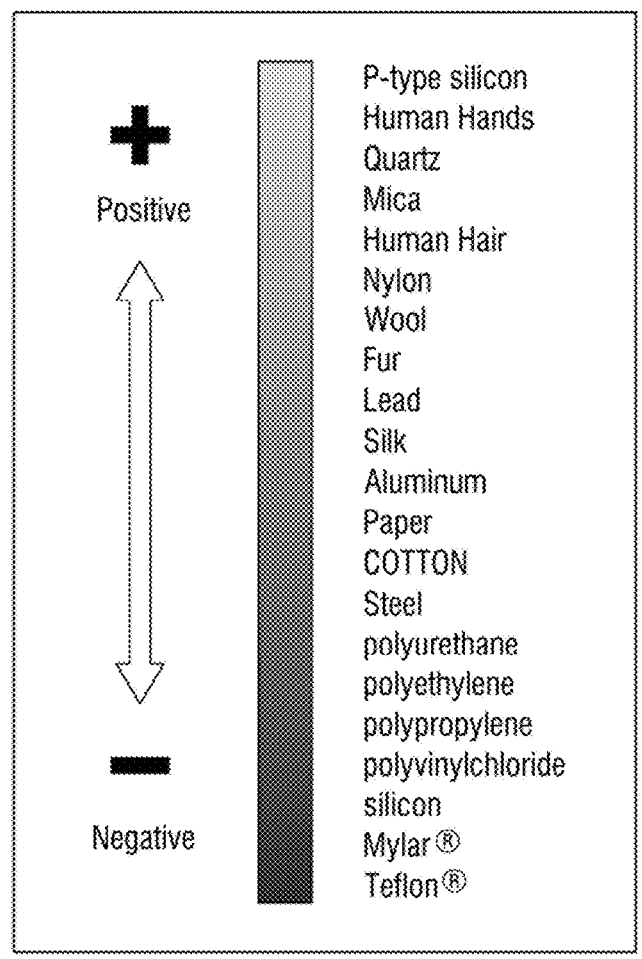
FIG. 2 is a diagram illustrating polarities of static electricity of some materials.
Figure 3:
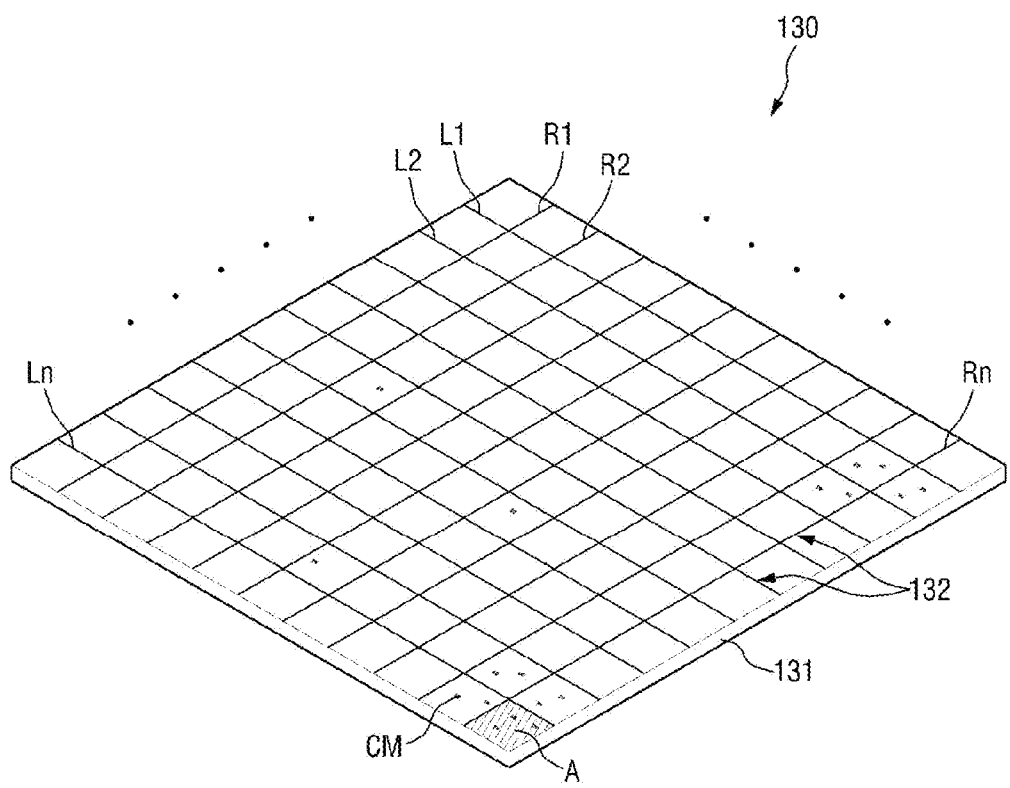
FIG. 3 is a perspective view illustrating an example of collection of contaminants on the contaminant measurement substrate of FIG. 1.

FIG. 1 is a perspective view of a contaminant measurement substrate according to an exemplary embodiment of the invention, FIG. 2 is a diagram illustrating polarities of static electricity of some materials, and FIG. 3 is a perspective view illustrating an example of collection of contaminants on the contaminant measurement substrate of FIG. 1.

Referring to FIG. 1, a contaminant measurement substrate 130 is used to measure contaminants that occur in a process of fabricating a substrate. Before actual processes are performed in a chamber providing a space in which the actual processes are performed, contaminants in the chamber are collected in advance to confirm which portion of the chamber the contaminants occur in.

The substrate may include a substrate for a display device. In an exemplary embodiment, the substrate may be a substrate for a display device, such as an organic light emitting display ("OLED"), a liquid crystal display ("LCD"), or a plasma display, for example. In an exemplary embodiment, the substrate may be a bare substrate, or a substrate including structures such as thin films or wirings thereon.

Further, in an exemplary embodiment, the substrate may be a substrate that includes one unit cell or a mother substrate that includes a plurality of unit cells. The mother substrate may be separated into cells by cutting. In addition, the substrate may be a single substrate or a laminated substrate in which two or more substrates are disposed to come in contact with each other or spaced apart from each other so that the substrates face each other.

The actual processes may include a substrate thin-film deposition process, a coating process, an assembling process, and the like, and the chamber may be in a vacuum state or in a non-vacuum state depending on the processes.

The contaminant measurement substrate 130 may include a base material 131 and laser marks 132.

The base material 131 may have a same size as a size of the substrate that is used in the actual processes, and may include a material that can collect the contaminants by an electrostatic force. That is, the base material 131 may include a material having a negative electrostatic polarity value that is smaller than that of the formation material of the chamber that provides a space in which the contaminants are to be measured. In an exemplary embodiment, referring to FIG. 2, when the chamber includes steel, the base material 131 may include polytetrafluoroethylene having the negative electrostatic polarity value that is smaller than that of the steel, for example. Accordingly, as illustrated in FIG. 3, the contaminants CM that occur due to splitting or aging of a portion of the chamber may be collected on the base material 131 by the electrostatic force.

In some exemplary embodiments, the base material 131 may include a color which matches but is not equal to a color of a formation material of the chamber. In an exemplary embodiment, when the chamber includes steel of which the color is silver, the base material 131 may include an opaque material such as polytetrafluoroethylene (e.g., Teflon®) which is white, for example. Accordingly, the contaminants CM of the chamber, which are collected on the base material 131, can be easily confirmed by the naked eye of a worker.

FIG. 1 illustrates that the planar shape of the base material 131 is rectangular, but the invention is not limited thereto, and it may differ depending on the planar shape of the substrate that is used in the actual processes.

The laser marks 132 may include a plurality of first lines L1 to Ln that are disposed in parallel along a first direction and a plurality of second lines R1 to Rn that are disposed in parallel along a second direction that crosses the first direction to define coordinates provided on the base material 131. Accordingly, the laser marks 132 may provide a reference for effectively preventing the contaminant measurement substrate 130 from being drawn into the chamber in a state where the upper/lower portions or the left/right portions thereof are reversed. In an exemplary embodiment, the laser marks 132 may be provided by scanning of the base material 131 with laser.

The laser marks 132 may define a plurality of unit areas A having a first area by the plurality of first lines L1 to Ln and the plurality of second lines R1 to Rn. Among the plurality of unit areas A, at least one unit area A may correspond to one of the plurality of unit cells of the substrate that is used in the actual processes. Accordingly, the laser marks 132 may provide a reference for grasping which unit area among the plurality of unit areas A on the base material 131, which corresponds to a respective unit cell of the substrate, the contaminants of the chamber are collected and located, and thus may grasp which unit cell area of the substrate used in the actual processes has an inferiority using unit areas among the plurality of unit areas A on the base material 131 in which a number of collected contaminants of the chamber exceeds the reference value.

When it is grasped that the inferiority may occur in a certain unit cell of the substrate, a worker may repair or replace the chamber by confirmation of the occurrence of the splitting or aging with respect to a portion of the chamber that is adjacent to the cell unit area of the contaminant measurement substrate 130 corresponding to the unit cell of the substrate, in which it is grasped that the inferiority may occur, in the case where the contaminant measurement substrate 130 is drawn into the chamber to collect the contaminants of the chamber. The cell unit area may include one unit area A, two unit areas A or three or more unit areas A.

Hereinafter, the laser marks having various shapes, which are applied to the contaminant measurement substrate as described above, will be described.

Figure 4:
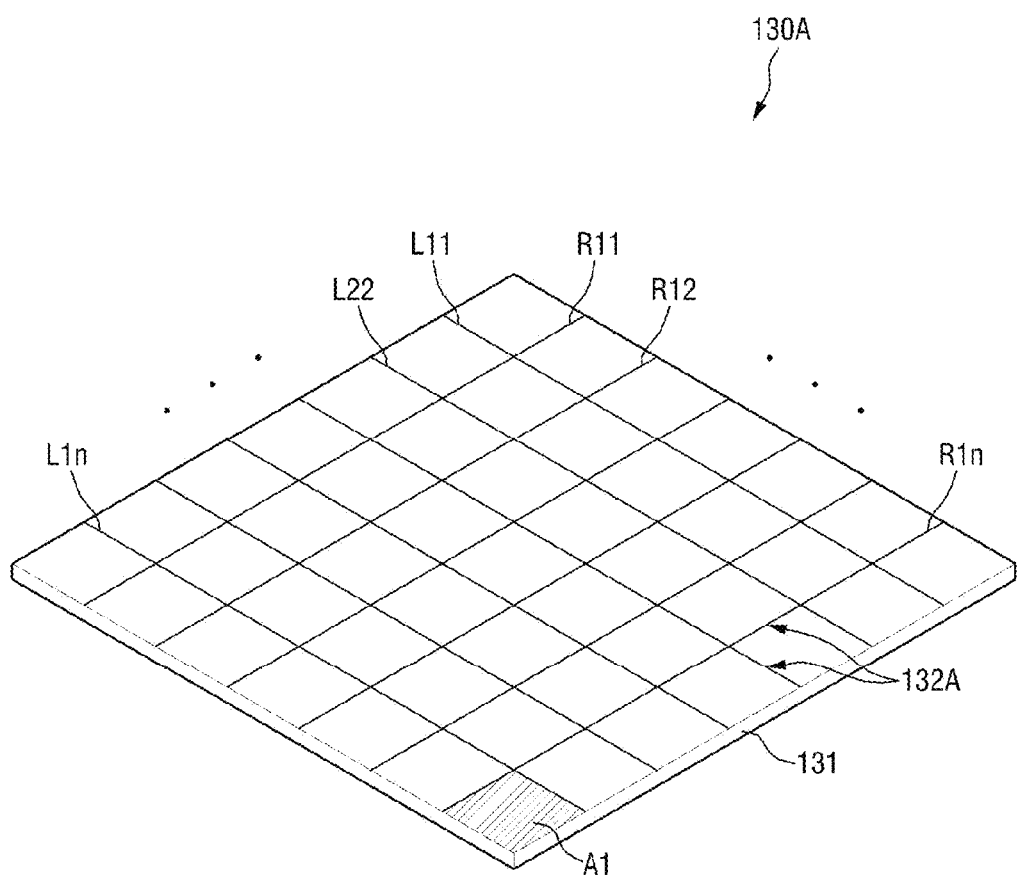
FIGS. 4 and 5 are perspective views illustrating various exemplary embodiments of laser marks on a contaminant measurement substrate according to the invention.
Figure 5:
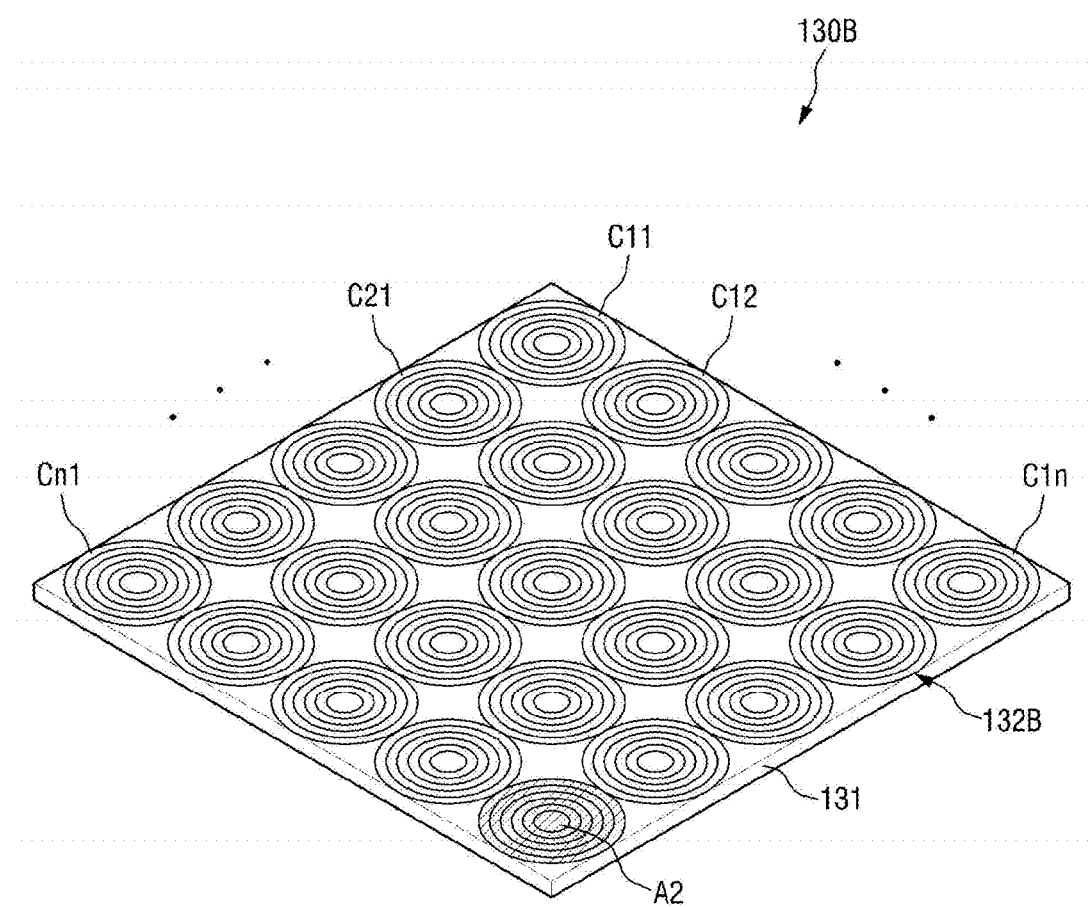

FIGS. 4 and 5 are perspective views illustrating laser marks on a contaminant measurement substrate according to various exemplary embodiments of the invention.

FIG. 4 exemplifies a contaminant measurement substrate 130A which has laser marks 132A including a plurality of first lines L11 to L1n that are disposed in parallel along a first direction and a plurality of second lines R11 to R1n that are disposed in parallel along a second direction that crosses the first direction to define coordinates provided on the base material 131 where the plurality of first lines L11 to L1n and the plurality of second lines R11 to R1n define a plurality of unit areas A1 having a second area. At least one of the plurality of unit areas A1 may correspond to one of the plurality of unit cells of the substrate that is used in the actual processes.

In an exemplary embodiment, the second area of one of the plurality of unit areas A1 may be larger than the first area of one of the plurality of unit areas A that are defined by the plurality of first lines L1 to Ln and the plurality of second lines R1 to Rn in FIG. 1. Accordingly, one unit cell which has a size that is larger than the size of two of the plurality of unit areas A illustrated in FIG. 1, for example, may correspond to two of the plurality of unit areas A1, for example. Therefore, it is possible to measure the contaminants of the chamber corresponding to the unit cells of the substrate having a large size.

Although not illustrated, in the same manner as the contaminant measurement substrate 130 in FIG. 1, the base material 131 of the contaminant measurement substrate 130A of FIG. 4 may also include a color which matches but is not equal to the color of the formation material of the chamber.

FIG. 5 exemplifies a contaminant measurement substrate 130B which has laser marks 132B including a plurality of groups of concentric circles Cij (where i and j are 1 to n, and n is a natural number) that are disposed along a first direction and a second direction that crosses the first direction. Here, the group of concentric circles C11 may be a group of concentric circles that is disposed at the first row in the first direction and at the first column in the second direction.

The laser marks 132B may define a plurality of unit areas A2 by the plurality of groups of concentric circles Cij. At least one of the plurality of unit areas A2 may correspond to one of the plurality of unit cells of the substrate that is used in the actual processes. Here, one unit area A2 may have a plurality of divided areas by a plurality of circular lines within the group of concentric circles. Accordingly, the laser marks 132B may provide a reference for sub-dividing and grasping which portion of a unit area A2, which corresponds to a respective unit cell of the substrate, among the plurality of unit areas on the base material 131 the contaminants of the chamber are collected.

Although not illustrated, in the same manner as the contaminant measurement substrate 130 in FIG. 1, the base material 131 of the contaminant measurement substrate 130B of FIG. 5 may also include a color which matches but is not equal to the color of the formation material of the chamber.

In the exemplary embodiments illustrated in FIGS. 1, 4 and 5, the number of contaminants of the chamber is measured by cell unit areas of the contaminant measurement substrate 130, 130A, or 130B corresponding to one of the plurality of unit cells of the substrate. However, when the substrate includes one unit cell, the number of contaminants of the chamber may be measured by unit areas of the contaminant measurement substrate. Therefore, in the case where the substrate includes one unit cell, it can be grasped which portion of the one unit cell the inferiority may occur in.

As described above, since the contaminant measurement substrate 130 according to an exemplary embodiment of the invention includes the base material 131 that can collect the contaminants and the laser marks 132 that define the coordinates provided on the base material 131, the contaminants of the chamber can be measured before the actual processes of the substrate, the occurrence position of the contaminants of the chamber can be grasped, and thus the occurrence cause of the contaminants of the chamber can be removed.

Accordingly, the contaminant measurement substrates 130, 130A and 130B according to the exemplary embodiments of the invention can effectively prevent the inferiority of the substrate that passes by the actual processes.

Next, an apparatus for fabricating a substrate according to another exemplary embodiment of the invention will be described.

Figure 6:
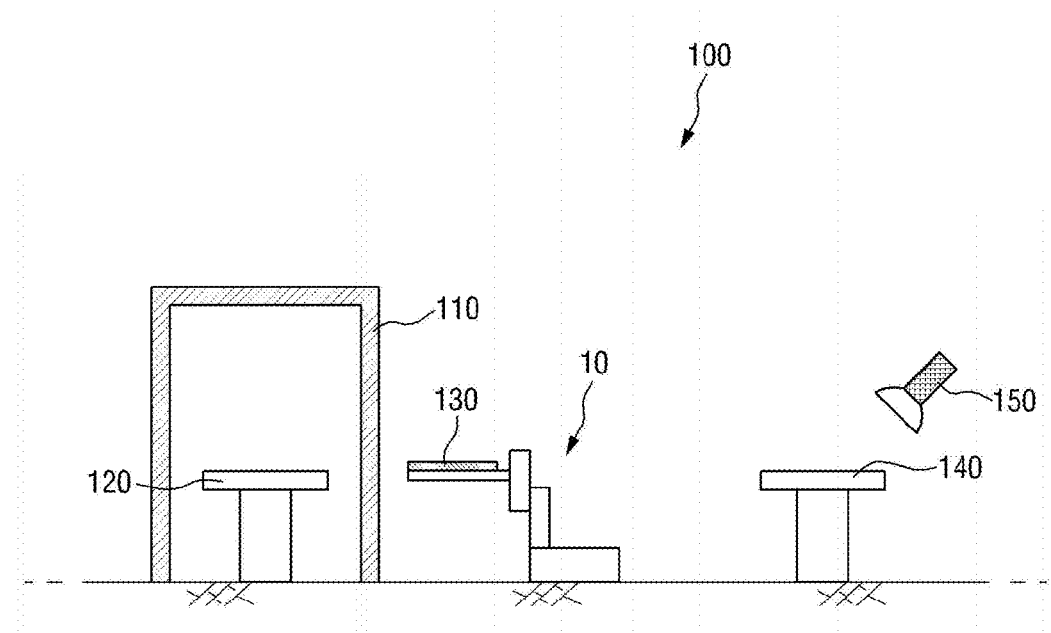
FIG. 6 is a cross-sectional view of another exemplary embodiment of an apparatus for fabricating a substrate according to the invention.

FIG. 6 is a cross-sectional view of an apparatus for fabricating a substrate according to another exemplary embodiment of the invention.

Referring to FIG. 6, an apparatus 100 for fabricating a substrate according to another exemplary embodiment of the invention may include a chamber 110, a first stage 120, a contaminant measurement substrate 130, a second stage 140, and a contaminant measurement light source 150.

The chamber 110 provides a space in which the actual processes are performed. The chamber may be in a vacuum state or in a non-vacuum state depending on the processes. In an exemplary embodiment, when the chamber 110 provides a space in which a substrate thin-film deposition process is performed, it may be in the vacuum state, for example. When the chamber 110 provides a space in which an assembling process is performed, it may be in the non-vacuum state.

The chamber 110 may include steel, but the invention is not limited thereto. When splitting or aging of a portion of the chamber 110 occurs in a state where the chamber 110 includes steel, for example, contaminants of the same material as the formation material of the chamber, that is, contaminants of a steel material may occur. Although FIG. 6 illustrates one chamber 110, a plurality of chambers may be provided depending on a kind of the substrate fabricating process.

A first stage 120 is disposed (e.g., installed) inside the chamber 110. The first stage 120 provides a space in which the contaminant measurement substrate 130 can be seated before the actual processes for the substrate are performed, and enables the contaminant measurement substrate 130 to collect the contaminants of the chamber 110. Further, the first stage 120 provides a space in which the substrate (e.g., substrate for a display device) can be seated during the actual processes for the substrate, and enables the actual processes to be performed on the substrate.

The contaminant measurement substrate 130 is used to measure the contaminants occurring in the substrate fabricating process, and collects the contaminants of the chamber 110 before the actual processes are performed in the chamber 110 to enable a worker to confirm which portion of the chamber 110 the contaminants occur in.

The contaminant measurement substrate 130 may be drawn into the chamber 110 or drawn out from the chamber 110 by a transport device 10 such as a robot. When a plurality of chambers 110 is provided, the contaminant measurement substrate 130 may be used to collect the contaminants of one chamber 100, and then may be used again to collect the contaminants of the other chamber 110 after being cleaned. In some exemplary embodiments, when a plurality of chambers 110 is provided, a number of contaminant measurement substrates 130 may be set to be equal to a number of chambers 110, and in this case, a plurality of contaminant measurement substrates 130 may be used to collect the contaminants of the plurality of chambers 110, respectively. Since the contaminant measurement substrate 130 has been described in detail, the duplicate description thereof will be omitted.

The second stage 140 is disposed (e.g., installed) outside the chamber 110. The second stage 140 may provide a space in which the contaminant measurement substrate 130 is seated, and enable a worker to confirm the contaminant measurement substrate 130 on which the contaminants of the chamber 110 are collected.

The contaminant measurement light source 150 is disposed on an upper portion of the second stage 140. The contaminant measurement light source 150 may irradiate the contaminant measurement substrate 130 seated on the second stage 140 with light to perform measurement of the contaminants of the chamber 110 from the contaminant measurement substrate 130. In an exemplary embodiment, the contaminant measurement light source 150 may be an ultraviolet light source.

In an exemplary embodiment, the measurement of the contaminants may be performed by the naked eye by confirming how much and which area of the contaminant measurement substrate 130, that is, which unit area, which corresponds to a respective unit cell of the substrate, the contaminants of the chamber 110 are located. Here, when the number of contaminants of the chamber 110 existing in a certain cell unit area exceeds the reference value, it can be grasped that the inferiority may occur in the unit cell that corresponds to the cell unit area, and a worker may repair or replace the chamber 110 by confirmation of the occurrence of the splitting or aging with respect to a portion of the chamber 110 that is adjacent to the cell unit area corresponding to the unit cell, in which it is grasped that the inferiority may occur, in the case where the contaminant measurement substrate 130 is drawn into the chamber to collect the contaminants of the chamber. Further, when it is confirmed that the number of contaminants of the chamber 110 existing in the respective unit area among the plurality of unit areas A, which corresponds to the respective unit cells of the substrate, is smaller than the reference value, a worker may draw the substrate (e.g., substrate for a display device) into the chamber 110 to perform the actual processes on the substrate.

As described above, since the apparatus 100 for fabricating a substrate according to the illustrated exemplary embodiment of the invention includes the contaminant measurement substrate 130, the contaminants of the chamber 110 can be measured before the actual processes of the substrate, the occurrence position of the contaminants of the chamber 110 can be grasped, and thus the occurrence cause of the contaminants of the chamber 110 can be removed.

Accordingly, the apparatus 100 for fabricating a substrate according to the illustrated exemplary embodiment of the invention can effectively prevent the inferiority of the substrate that passes by the actual processes.

Next, an apparatus 200 for fabricating a substrate according to the illustrated exemplary embodiment of the invention will be described.

Figure 7:
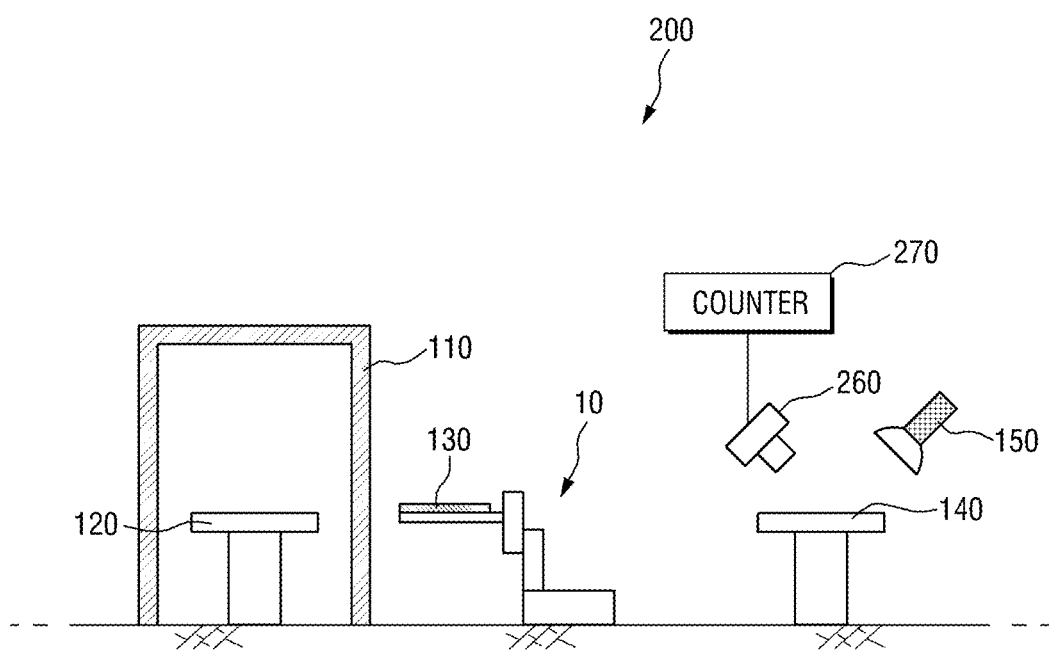
FIG. 7 is a cross-sectional view of another exemplary embodiment of an apparatus for fabricating a substrate according to the invention.

FIG. 7 is a cross-sectional view of an apparatus for fabricating a substrate according to another exemplary embodiment of the invention.

An apparatus 200 for fabricating a substrate according to the illustrated exemplary embodiment of the invention has the same configuration as the configuration of the apparatus 100 for fabricating a substrate of FIG. 6 except for the point that the apparatus 200 includes an imaging device 260 and a counter 270. Accordingly, in the apparatus 200 for fabricating a substrate according to the illustrated exemplary embodiment of the invention, explanation will be made around the imaging device 260 and the counter 270.

Referring to FIG. 7, the apparatus 200 for fabricating a substrate according to the illustrated exemplary embodiment of the invention may include a chamber 110, a first stage 120, a contaminant measurement substrate 130, a second stage 140, a contaminant measurement light source 150, an imaging device 260 and a counter 270.

The imaging device 260 is disposed on an upper portion of the second stage 140. The imaging device 260 may capture an image of the contaminant measurement substrate 130 seated on the second stage 140 to enable the counter 270 to perform measurement of the contaminants. In an exemplary embodiment, the imaging device 260 may be a camera or an optical microscope, for example.

The counter 270 may receive the image of the contaminant measurement substrate 130 that is captured by the imaging device 260, and count the contaminants of the chamber 110 collected on the contaminant measurement substrate 130. In an exemplary embodiment, the counter 270 may be programmed to confirm amounts and locations of the contaminants on the contaminant measurement substrate 130. That is, the counter 270 may be programmed to confirm locations of unit area, which corresponds to the respective unit cells of the substrate, containing the contaminants of the chamber 110 and the amounts of the contaminants by comparing a pre-stored original image (image in which no contaminant exists) of the contaminant measurement substrate 130 with the image received from the imaging device 260. Although not illustrated, the counter 270 may include a display for displaying data obtained by grasping the amounts and the locations of the contaminants of the chamber 110 on the contaminant measurement substrate 130.

Further, the counter 270 compares the number of contaminants of the chamber 110 existing in the respective unit area among the unit areas A, which corresponds to the respective unit cells of the substrate, with a reference value. When it is confirmed that the number of contaminants of the chamber 110 existing in a certain cell unit area exceeds the reference value, a warning signal indicating that the inferiority may occur in the unit cell that corresponds to the cell unit area may be output. In this case, a worker may repair or replace the chamber 110 by confirmation of the occurrence of the splitting or aging with respect to a portion of the chamber 110 that is adjacent to the cell unit area corresponding to the unit cell, in which it is grasped that the inferiority may occur, in the case where the contaminant measurement substrate 130 is drawn into the chamber 110 to collect the contaminants of the chamber 110.

The counter 270 compares the number of contaminants of the chamber 110 existing in the respective unit area among the plurality of unit areas A, which corresponds to the respective unit cell of the substrate, with the reference value, and when it is confirmed that the number of contaminants of the chamber 110 existing in the respective unit area is smaller than the reference value, a process signal for performing the actual processes on the substrate is output. Accordingly, a worker may draw the substrate (e.g., substrate for a display device) into the chamber 110 to perform the actual processes on the substrate.

Next, a method for fabricating a substrate according to an exemplary embodiment of the invention will be described.

Figure 8:
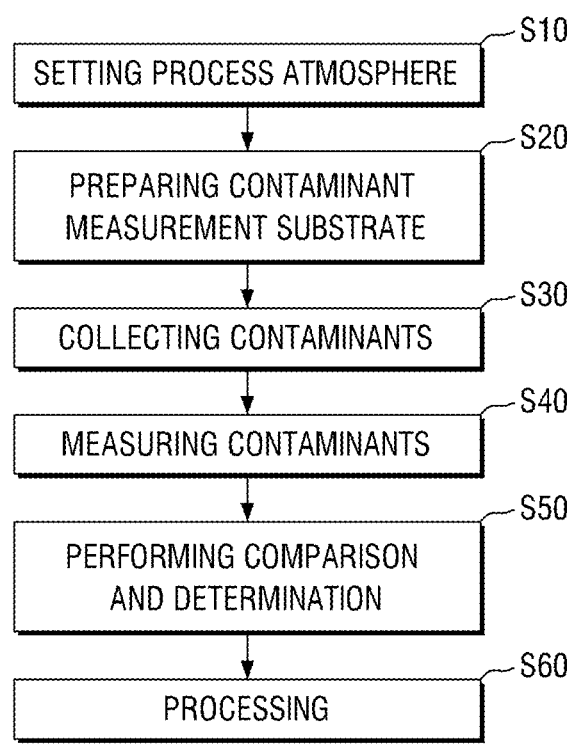
FIG. 8 is a flowchart of a method for fabricating an exemplary embodiment of a substrate according to the invention.

FIG. 8 is a flowchart of a method for fabricating a substrate according to an exemplary embodiment of the invention, and FIGS. 9 to 15 are cross-sectional views explaining the method for fabricating a substrate of FIG. 8.

Referring to FIG. 8, the method for fabricating a substrate according to an exemplary embodiment of the invention includes setting a process atmosphere (S10), preparing a contaminant measurement substrate (S20), collecting contaminants (S30), measuring the contaminants (S40), comparing and determining (S50), and processing (S60).

Figure 9:
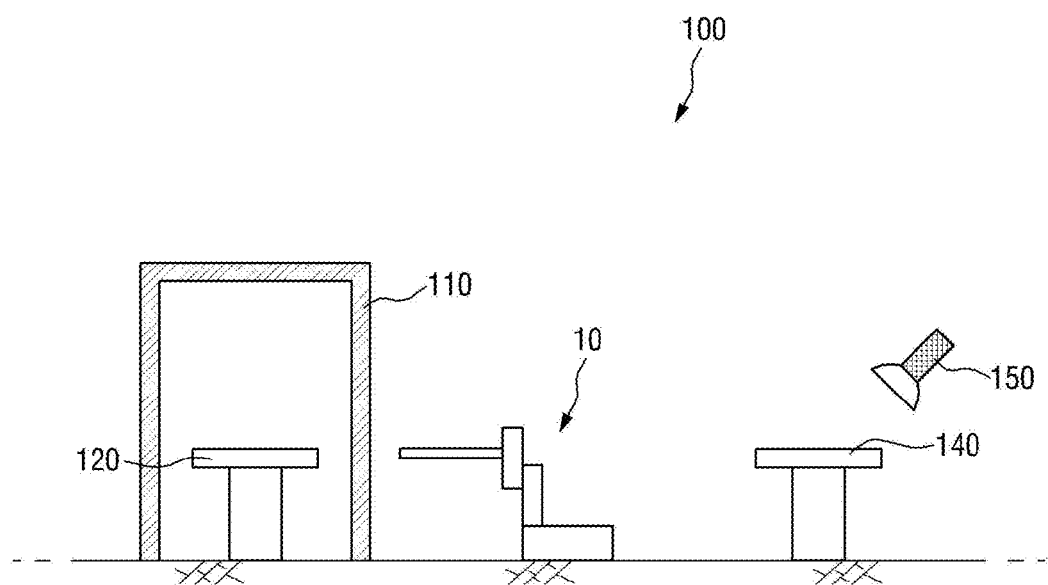
FIGS. 9 to 15 are cross-sectional views explaining the method for fabricating a substrate of FIG. 8.

Referring to FIG. 9, the setting of the process atmosphere (S10) sets the process atmosphere of the chamber 110 providing a space in which processes are performed. The setting of the process atmosphere of the chamber 110 may include making the chamber 110 in a vacuum state or in a non-vacuum state depending on a kind of a substrate fabricating process.

Figure 10:
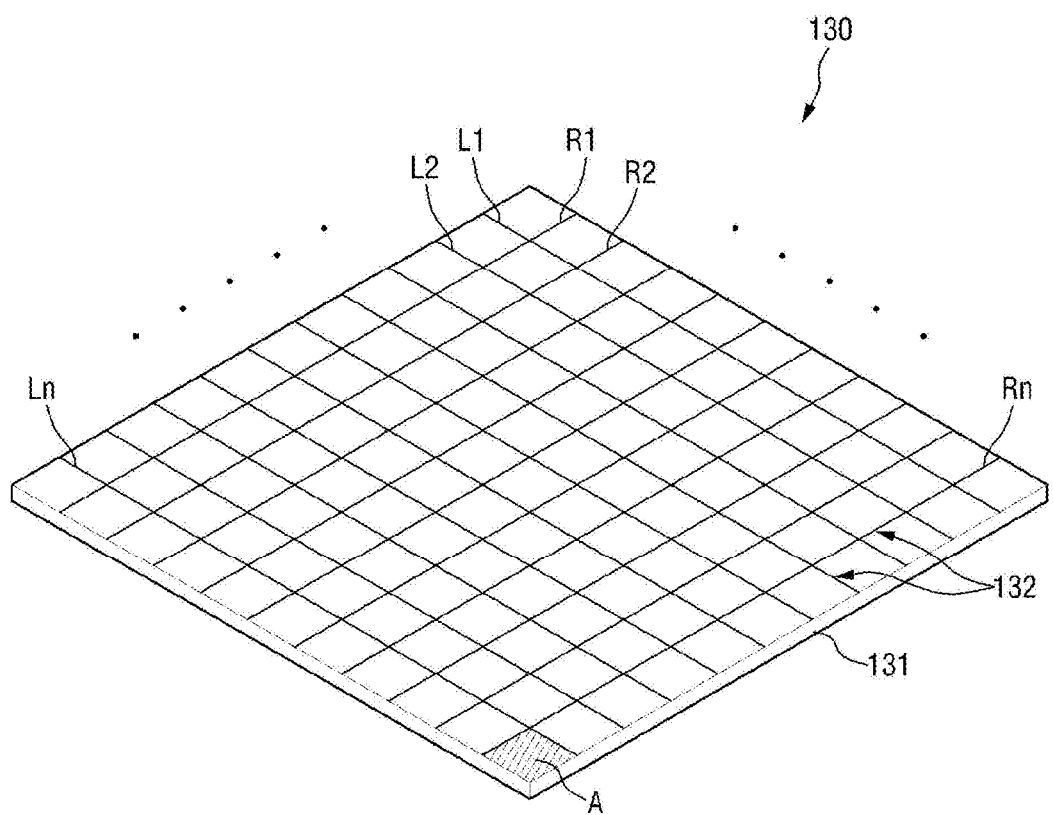

Referring to FIG. 10, the preparing of the contaminant measurement substrate (S20) prepares the contaminant measurement substrate 130 including a base material 131 collecting contaminants and laser marks 132 defining coordinates provided on the base material 131.

The preparing of the contaminant measurement substrate (S20) may include providing the contaminant measurement substrate 130 including a material having a negative electrostatic polarity value which is smaller than that of a formation material of the chamber 110. Further, the preparing of the contaminant measurement substrate (S20) may include providing the contaminant measurement substrate 130 having a color that matches a color of the formation material of the chamber 110. Since the contaminant measurement substrate 130 has been described in detail, the duplicate description thereof will be omitted.

Figure 11:
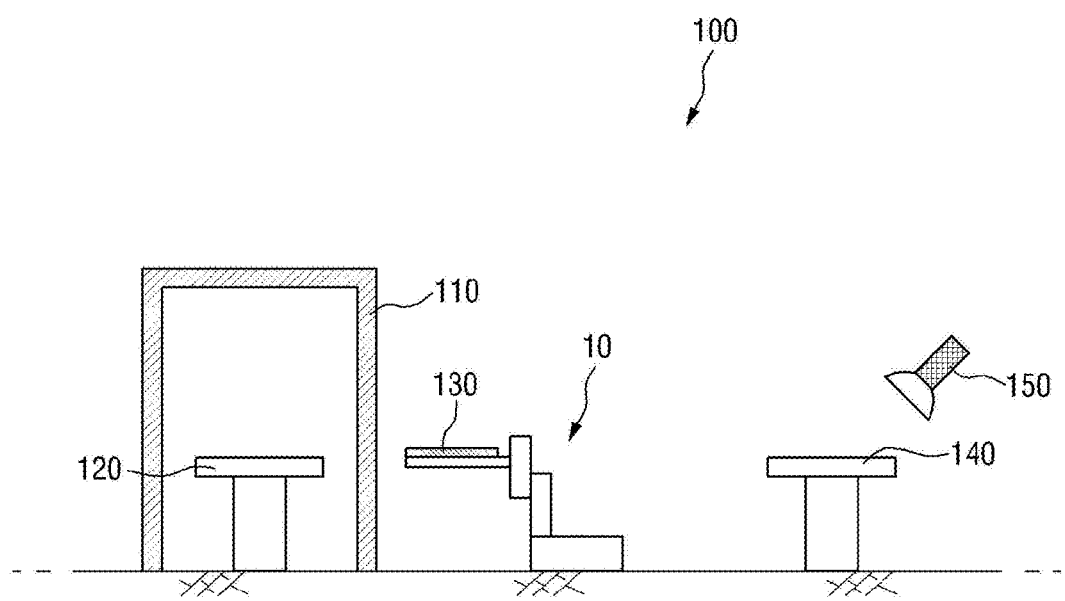

As illustrated in FIG. 11, in an exemplary embodiment, the prepared contaminant measurement substrate 130 may be transported toward the chamber 110 by a transport device 10 such as a robot.

Figure 12:
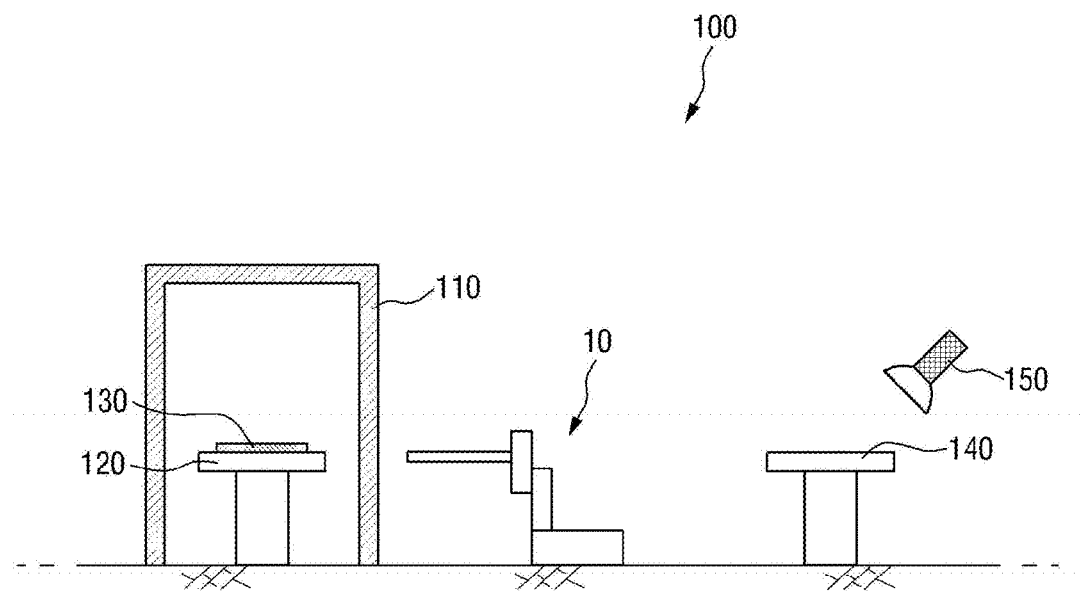
Figure 13:
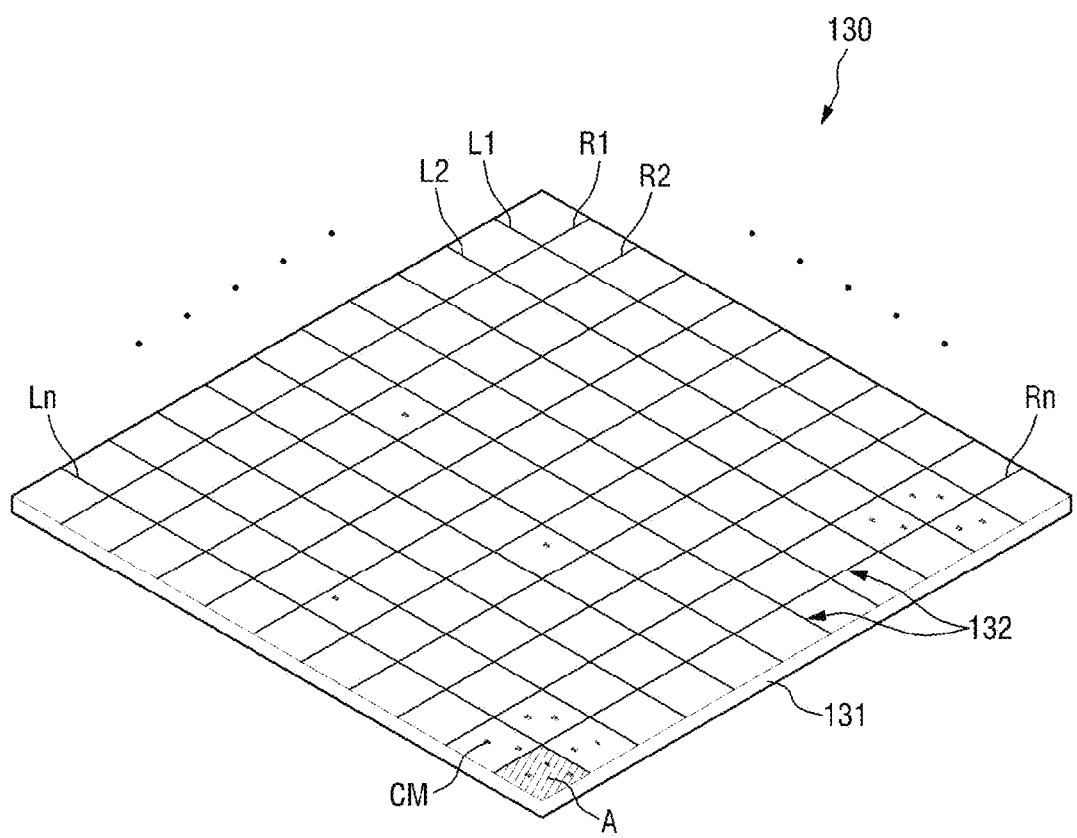

Referring to FIG. 12, the collecting of the contaminants (S30) collects the contaminants of the chamber 110 by seating the contaminant measurement substrate 130 on a first stage 120 which is disposed (e.g., installed) inside the chamber 110. In an exemplary embodiment, the collecting of the contaminants CM of the chamber 110 may be performed, for example, as shown in FIG. 13. In an exemplary embodiment, the collecting of the contaminants CM of the chamber 110 may be performed for a same time as an actual processing time.

Figure 14:
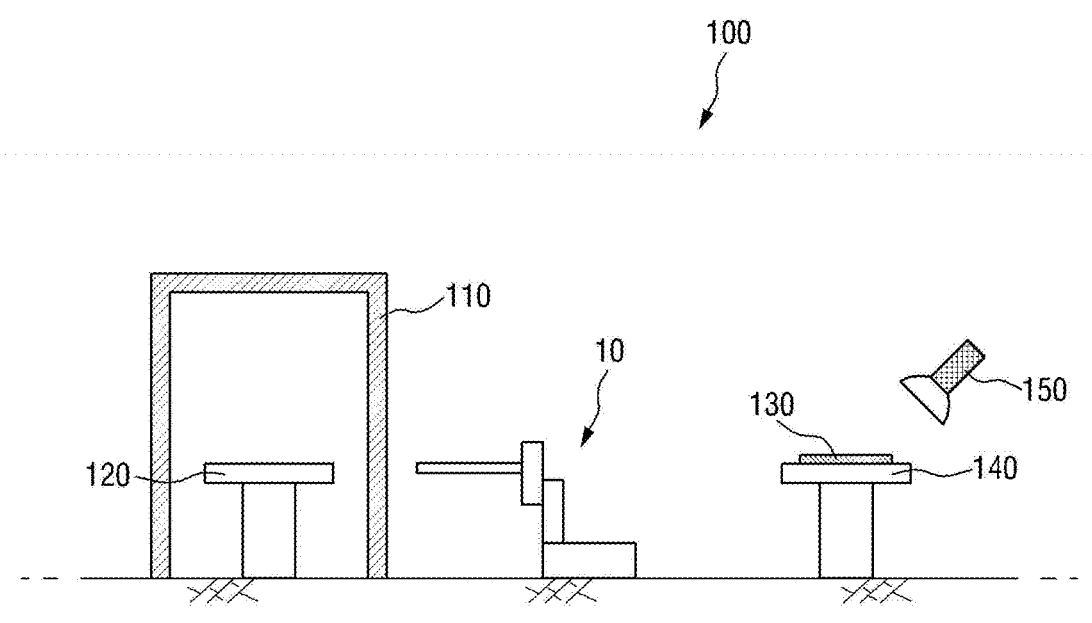

Referring to FIG. 14, the measuring of the contaminants (S40) measures the contaminants of the chamber 110 collected with respect to a plurality of unit areas A that is defined by laser marks 132 in FIG. 13 from the contaminant measurement substrate 130 by seating the contaminant measurement substrate 130 on a second stage 140 which is disposed (e.g., installed) outside the chamber 110 and irradiating the contaminant measurement substrate 130 with light using the contaminant measurement light source 150.

In an exemplary embodiment, the measurement of the contaminants may be performed by the naked eye by confirming amounts and locations of the contaminants on the contaminant measurement substrate 130. That is, the measurement of the contaminants may be performed by confirming locations of unit area among the plurality of unit areas A, which corresponds to the respective unit cell of the substrate, containing the contaminants of the chamber 110 and the amounts of the contaminants. In the case of using the imaging device 260 (refer to FIG. 7) disposed on the upper portion of the second stage 140 to capture an image of the contaminant measurement substrate 130 and the counter receiving the image of the contaminant measurement substrate 130 captured by the imaging device and counting the contaminants of the chamber 110 that are collected on the contaminant measurement substrate 130, the measurement of the contaminants of the chamber 110 may be performed by the counter 270 (refer to FIG. 7).

The comparing and determining (S50) compares the number of contaminants CM of the chamber 110 existing in a unit area among the plurality of unit areas A in FIG. 13, which corresponds to the respective unit cell of the substrate, with the reference value, and determines whether the number of contaminants CM of the chamber 110 existing in the respective unit area exceeds the reference value.

In an exemplary embodiment, the comparing and determining (S50) may be performed by a worker when the measurement of the contaminants of the chamber 110 is performed by the naked eye in the measuring of the contaminants (S40). In an exemplary embodiment, the comparing and determining (S50) may be performed by the counter 270 (refer to FIG. 7) when the measurement of the contaminants of the chamber 110 is performed by the counter 270 in the measuring of the contaminants (S40).

Figure 15:
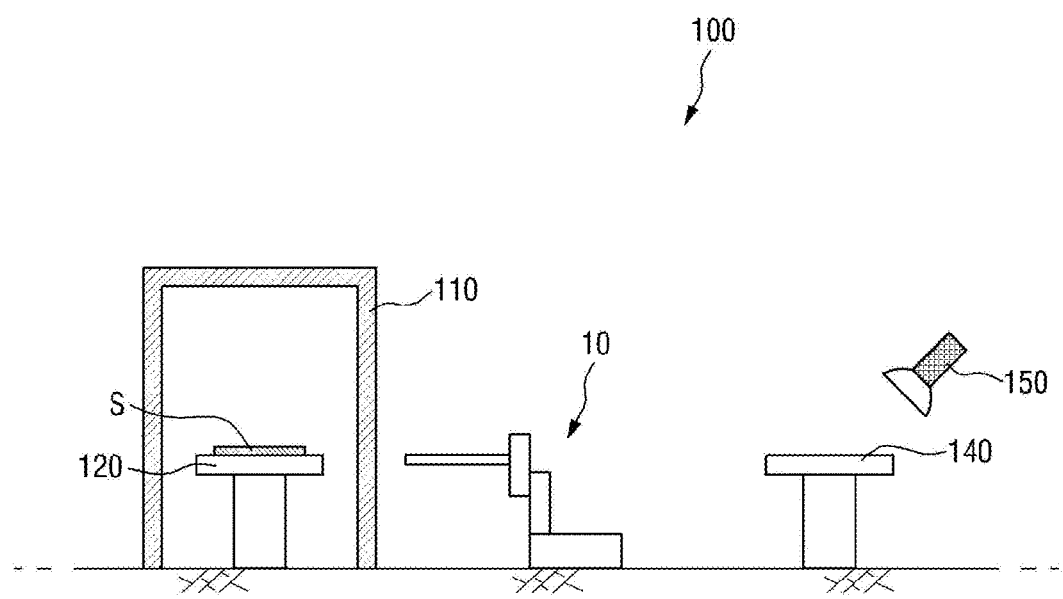

When it is grasped that the number of contaminants CM of the chamber 110 existing in a certain cell unit area A (refer to FIG. 13) exceeds the reference value so that the inferiority may occur in the unit cell of the substrate that corresponds to the cell unit area in the comparing and determining (S50), then the processing (S60) process to confirm a portion of the chamber 110 that is adjacent to the cell unit area corresponding to the grasped unit cell, in which it is grasped that the inferiority may occur, and when it is grasped that the number of contaminants CM of the chamber 110 existing in the respective unit area is smaller than the reference value, the processing (S60) process to draw the substrate (e.g., substrate for a display device) as shown in FIG. 15 into the chamber 110 to perform the actual processes on the substrate.

In the processing (S60), a worker may directly confirm the result that is determined by the naked eye in the comparing and determining (S50) or may receive the result that is determined by the counter in the comparing and determining (S50) to perform the corresponding process.

In concluding the detailed description, those skilled in the art will appreciate that many variations and modifications can be made to the preferred exemplary embodiments without substantially departing from the principles of the invention. Therefore, the disclosed preferred exemplary embodiments of the invention are used in a generic and descriptive sense only and not for purposes of limitation.

What is claimed is:

1. An apparatus for fabricating a substrate, comprising:
   a chamber providing a space in which processes are performed;
   a contaminant measurement substrate including:
      a base material configured to collect contaminants, and
      laser marks on the base material and defining coordinates of the base material;
      a first stage disposed inside the chamber, and upon which the contaminant measurement substrate is seated during collection of the contaminants of the chamber;
      a second stage disposed outside the chamber, and upon which the contaminant measurement substrate is seated during measurement of the contaminants of the chamber collected on the contaminant measurement substrate; and
   a contaminant measurement light source disposed on an upper portion of the second stage and configured to irradiate the contaminant measurement substrate seated on the second stage with light during the measurement of the contaminants of the chamber collected on the contaminant measurement substrate.

2. The apparatus for fabricating a substrate of claim 1, wherein the laser marks comprise:
   a plurality of first lines disposed in parallel along a first direction; and
   a plurality of second lines disposed in parallel along a second direction which crosses the first direction.

3. The apparatus for fabricating a substrate of claim 1, wherein the laser marks comprise a plurality of groups of concentric circles disposed along a first direction, and a second direction which crosses the first direction.

4. The apparatus for fabricating a substrate of claim 1, wherein
   the chamber includes steel, and
   the base material includes a material having a negative electrostatic polarity value which is smaller than that of the steel.

5. The apparatus for fabricating a substrate of claim 1, wherein the base material includes polytetrafluoroethylene.

6. The apparatus for fabricating a substrate of claim 1, wherein the contaminant measurement substrate has a color which matches a color of the chamber.

7. The apparatus for fabricating a substrate of claim 1, wherein the contaminant measurement light source is an ultraviolet light source.

8. The apparatus for fabricating a substrate of claim 1, further comprising:
   an imaging device disposed on the upper portion of the second stage and configured to capture an image of the contaminant measurement substrate seated on the second stage; and
   a counter which is configured to count the contaminants of the chamber from the image of the contaminant measurement substrate.

9. A method for fabricating a substrate, the method comprising:
   preparing a contaminant measurement substrate including a base material configured to collect contaminants, and laser marks on the base material and defining a plurality of unit areas on the contaminant measurement substrate respectively corresponding to unit cells of the substrate;
   seating the contaminant measurement substrate on a first stage which is disposed inside a chamber which provides a space in which processes are performed, and collecting the contaminants of the chamber;

seating the contaminant measurement substrate on a second stage which is disposed outside the chamber, and measuring the contaminants of the chamber which are collected with respect to the plurality of unit areas, by irradiating the contaminant measurement substrate with light using a contaminant measurement light source; and comparing a number of the contaminants of the chamber, which exist in a respective unit area among the plurality of unit areas, with a reference value, and determining whether the number of the contaminants of the chamber existing in the respective unit area exceeds the reference value.

10. The method for fabricating a substrate of claim 9, wherein the chamber includes steel, and the base material includes a material having a negative electrostatic polarity value which is smaller than that of steel.

11. The method for fabricating a substrate of claim 9, wherein the contaminant measurement substrate has a color which matches a color of the chamber.

12. The method for fabricating a substrate of claim 9, wherein the measuring the contaminants of the chamber comprises preparing an ultraviolet light source as the contaminant measurement light source.

13. The method for fabricating a substrate of claim 9, wherein the measuring the contaminants of the chamber comprises:

capturing an image of the contaminant measurement substrate, using an imaging device disposed on an upper portion of the second stage; and counting the contaminants of the chamber from the image of the contaminant measurement substrate, using a counter.

14. The method for fabricating a substrate of claim 9, further comprising, when a number of the contaminants of the chamber existing in the respective unit area exceeds the reference value in the comparing and determining, confirming a portion of the chamber which is adjacent to the respective unit area, and when a number of the contaminants of the chamber existing in the respective unit area is smaller than the reference value, drawn the substrate into the chamber to perform the processes on the substrate.

15. The method for fabricating a substrate of claim 14, wherein the substrate is a substrate for a display device.

16. A contaminant measurement substrate comprising:

a base material which collects contaminants; and laser marks on the base material defining coordinates of the base material which further define a plurality of unit areas respectively corresponding to unit cells of the substrate for comparing a number of the contaminants which exist in a respective unit area among the plurality of unit areas.

17. The contaminant measurement substrate of claim 16, wherein the laser marks comprise:

a plurality of first lines disposed in parallel along a first direction, and a plurality of second lines disposed in parallel along a second direction which crosses the first direction.

18. The contaminant measurement substrate of claim 16, wherein the laser marks comprise a plurality of groups of concentric circles disposed along a first direction, and a second direction which crosses the first direction.

19. The contaminant measurement substrate of claim 16, wherein the base material includes a material having a negative electrostatic polarity value which is smaller than that of steel.

20. The contaminant measurement substrate of claim 16, wherein the base material includes polytetrafluoroethylene.

* * * * *